United States Patent [19]

Macy

[11] Patent Number: 4,710,370

[45] Date of Patent: Dec. 1, 1987

[54] METHOD FOR DETECTION OF CUSHING'S SYNDROME IN DOMESTIC ANIMALS

[75] Inventor: Dennis W. Macy, Fort Collins, Colo.

[73] Assignee: Colorado State University Research Foundation, Fort Collins, Colo.

[21] Appl. No.: 727,367

[22] Filed: Apr. 25, 1985

[51] Int. Cl.$^4$ .............................................. A61K 49/00
[52] U.S. Cl. ..................................................... 424/9
[58] Field of Search ........................................... 424/9

[56] References Cited

PUBLICATIONS

Taminato, et al.–Chem. Abst., vol. 83, (1975), p. 41118b.
Johnson, R. K.: Insulinoma in the Dog, Vet Clin. North Am., 7(3):, 629–635.
Behrans, O. K. and Broner, W.: Glucagon, Vitamins and Hormones, vol. XVI-16, 263–301, Academic Press, New York, (1958).
Kemppainen, R. J., et al., Adrenocortical Suppression in the Dog Given A Single Intramuscular Dose of Prednisone or Triamcinoline Acetonide, Am J Vet Res, vol. 42, No. 5, 204–206.
Wellman, M. L., et al., Immunoassay for the Steroid-Induced Isoenzyme of Alkaline Phosphatase in the Dog, Am J Vet Res, vol. 43, 1200–1204.
Adrenocortical Suppression in the Dog After A Single Dose of Methylprednisolone Acetate, Kemppainen, R. J., et al., AM J Vet Res, vol. 42, No. 5, 822–824.
Sequential Morphologic and Clinicopatholic Alterations in Dogs with Experimentally Induced Glucocorticoid Hepatopathy, Babylak, S. F., et al., AM J Vet Res, vol. 42, No. 5, 1310–1317.

*Primary Examiner*—Sam Rosen
*Attorney, Agent, or Firm*—Dorr, Carson, Sloan and Peterson

[57] ABSTRACT

A method for the detection of Cushing's syndrome in domestic animals is provided by first injecting glucagon into an animal suspected of having Cushing's syndrome and then monitoring the animal's blood glucose levels against an appropriate control over a two hour period. A blood glucose value above about 295 mg/dl is diagnostic for Cushing's syndrome.

5 Claims, 1 Drawing Figure

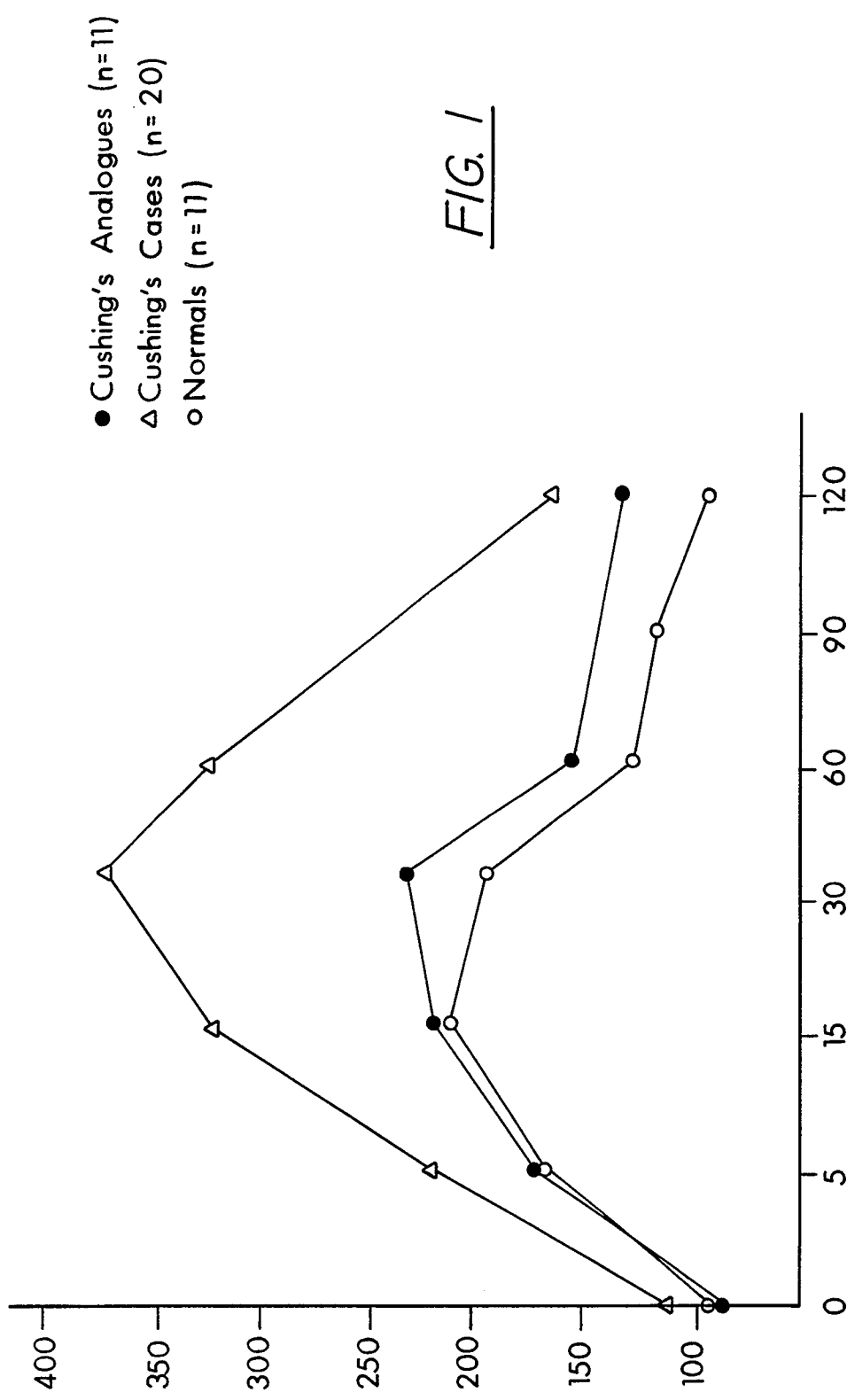

METHOD FOR DETECTION OF CUSHING'S SYNDROME IN DOMESTIC ANIMALS

BACKGROUND OF THE INVENTION

1. Field of the Invention

This invention relates generally to chemical methods for diagnosing Cushing's syndrome in domestic animals, particularly dogs and horses. More specifically, this invention relates to methods for detecting Cushing's syndrome based upon chemical analysis of hepatic functions. Central to any such chemical analysis is an understanding of the terms Cushing's syndrome, glycogen, glycogenesis, glycogenolysis and glucocorticoids.

Cushing's syndrome. Cushing's syndrome is a disease condition caused by the excessive production of corticosteroids by the adrenal cortex. The condition is often due to tumor or hyperplasia of either the pituitary gland or the adrenal cortex itself.

Glycogen. Glycogen is the chief storage form of carbohydrate in animals and is analogous to starch in plants. The principle organ in which glycogen is stored in the body is the liver. The process of glycogen synthesis (glycogenesis), and that of its breakdown (glycogenolysis) is known to proceed by two separate pathways.

Glycogenesis. The initial reaction required for the entrance of glucose into the series of metabolic reactions which culminate in the synthesis of glycogen is phosphorylation of glucose at the C-6 position. Glucose is phosphorylated by adenosine triphosphate (ATP) in the liver by an irreversible enzymatic reaction which is catalyzed by a specific glucokinase. This undirectional phosphorylation permits the accumulation of glucose in the liver cell since the phosphorylated sugars do not pass freely in and out of the cell in contrast to the readily diffusable free sugars. The trapped glucose-6-phosphatase is converted to glucose-1-phosphatase, a reaction catalyzed by phosphoglucomutase. Glycogen is synthesized from the glucose-1-phosphate through reactions involving the formation of uridine derivatives. In the presence of polysaccharide primers and the enzyme glycogen synthetase, the glucose moiety of the urine derivatives is linked to the polysaccharide. Through repeated transfers of glucose, the polysaccharide chain is eventually lengthened until a glycogen molecule is formed.

Glycogenolysis. The breakdown of liver glycogen to glucose takes place by a second pathway. In the presence of inorganic phosphate, the glucose linkage of glycogen is successfully broken by active phosphorylases. Epinephrine and glucagon influence the phosphorolytic breakdown of glycogen to glucose. The phosphorolytic enzyme exists in the liver in two forms: an active form designated liver phosphorylase (LP) which contains phosphate and an inactive form designated dephosphorylase (dephospho-P), in which phosphate has been removed. The transformation between the active and the inactive forms are catalyzed by specific kinase enzymes. Normally the level of LP is low and the epinephrine and glucagon shifts the equilibrium toward a higher level of LP. The net result is an increased phosphorolytic breakdown of glycogen to glucose. A hyperglycemia is observed clinically following the injection of either of these two hormones.

Glucocorticoids. Glucocorticoids promote liver glycogen storage. This increase in liver glycogen storage has been attributed to glucocorticoid enhancement of gluconeogenesis, hyperglycemia, decreased glycogenolysis and decreased glucose oxidation.

Glucagon. Glucagon has been used in certain diagnostic procedures as well as in various pharmaceutical treatments. It is a polypeptide secreted by the alpha cells on the pancreas. The primary structure of porcine, bovine and human glucagon are identical. Glucagon is produced as a by-product of insulin production from pork and beef pancreases. Injections of glucagon are known to elevate blood glucose levels by causing hepatic glycogenolysis. Furthermore, it is known that under standardized conditions, glucagon induces reproducable hyperglycemia in test animals.

However, despite the knowledge of glycogenesis and glycogenolysis, it has not been heretofore fully appreciated that the intravenous administration of glucagon (glucagon tolerance test) may be used to detect the excessive storage of liver glycogen which can be diagnostic of Cushing's syndrome.

2. Prior Art

Cushing's syndrome in the dog is frequently a diagnostic challenge to the practicing veterinarian. Cushing's must be considered in any patient presented with histories of increased water consumption, urination, elevation in serum alkaline phosphatase levels or symmetrical alopecia. However, none of these signs are diagnostic for Cushing's, and in fact often are associated with many other more common clinical entities. Because the treatment for Cushing's is often associated with significant cost and occasionally high morbidity, a definitive diagnosis of Cushing's is necessary before treatment.

The clinical signs associated with Cushing's are caused by increased levels of endogenous cortisol. The current method of diagnosing Cushing's includes the ACTH stimulation test and/or the dexamethasone suppression test. The ACTH stimulation test is performed by taking blood for a baseline cortisol assay followed by the administration of ACTH and again collecting blood for cortisol assays 1-3 hours after the administration of the stimulating hormone. The Cushing's animal should have an exaggerated cortisol level following ACTH administration. The second most commonly employed test for the diagnosis of Cushing's is the dexamethasone suppression test. Again, blood samples are collected for baseline cortisol values and dexamethasone is administered. Blood is collected twice for cortisol assays, once at 3 hours and again at 8 hours. Normal animal cortisols become significantly depressed following dexamethasone therapy; Cushing's patients do not.

Both the ACTH stimulation test and dexamethasone suppression test require assays for blood cortisol. These are generally radioimmune assays and are not run in veterinarian's offices and must be packaged and mailed to specialized laboratories for analysis. These assays also are relatively expensive. In addition, these individual tests are associated with approximately 20% false negative results and therefore they are frequently combined in confirming the diagnosis of Cushing's and thereby further raising the outside lab charges. Hence, the principle disadvantages of these tests are their high cost, slow turnaround, cumbersome sample preparation procedures and false negatives. Consequently, any new test for Cushing's which is sensitive, reliable, economic and capable of in-house utilization in short time periods would be of great practical value to veterinary medicine. In order to obviate these problems, applicant has developed a safe, reliable test for diagnosis of Cushing's syndrome. Applicant's test is a heretofore unappreciated application of the glucagon tolerance test. Those skilled in the art will, of course, appreciate that variations of this test have been used to diagnose other pathologies. For example, glucagon tolerance test has been used in the dog to differentiate pancreatic tumor-bearing dogs in which insulin release is stimulated by the transient hyperglycemia product following glucagon administration; blood insulin levels are then measured. See Johnson RK: Insulinoma in the dog. Vet Clin North Am 7(3): 629-635, (1977). The cat has also been used as an in vivo means of assaying small quantities of glucagon. See Behrens OK, Broner W: Glucagon, Vitamin, and Hormone, vol XVI-16: 263-301, Academic Press, New York (1958). See also, Roberts, Steven M., et al., Effect of Ophthalmic Prednisolone Acetate on the Canine Adrenal Gland and Hepatic Function, AM. J. Vet. Res., Vol. 45, No. 9 (September 1984).

SUMMARY OF THE INVENTION

The methods and devices of this invention are based upon the fact that Cushing's syndrome results from excessive glucocorticoid production by the adrenal glands. Excessive levels of glucocorticoids act to increase hepatic glycogen storage and gluconeogenesis and to decrease glucose uptake in the peripheral tissue. Such glycogen deposition is increased in both fasted and fed animals. The increased glycogen deposition is believed to be the result of corticosteroid induced glycogen synthetase activity due to blockage of the inhibitory affect of glycogen phosphorylase "A" on glycogen synthetase. This enzyme converts glycogen synthetase from the inactive "A" form to the active "B" form. Glycogen breakdown may also be inhibited as a result phosphorylase "A" inactivation. In any case, glucagon stimulates the formation of cyclic AMP from ATP in the liver and leads to activation of phosphorylase, the rate-limiting enzyme in the conversion of glycogen to glucose. Although other changes may also occur, the glucagon induced rise in blood glucose concentration upon which this test is based is believed to be principally a result of glycogenolysis. My test is therefore an indirect measure of hepatic glycogen accumulation normally associated with supraphysiological levels of glucocorticoids. The test involves measuring blood glucose levels at various times, e.g., 0, 5, 15, 30, 60 and 120 minutes, over about a two hour period following intravenous injection of glucagon. The time period around 30 minutes after administration of glucagon can be a particularly important period in this test methodology since the greatest differentials between normal blood glucose levels and the elevated levels resulting from glucagon administration tend to occur around this point in time (See FIG. 1). The test is technically simple, economically inexpensive and, as indicated by later portions of this patent application, extremely sensitive. The test may be used as a preliminary screening test in the field, or it may be used in conjunction with other tests carried out in laboratories (e.g., ACTH stimulation tests and/or high and low dexamethasone suppression tests). More preferably, however, the test can be used as an independent, conclusive test in its own right in field test situations. Diagnostic procedures, as well as kits containing premeasured glucagon doses (i.e., for dog, horses etc.) to carry them out, can be readily prepared based upon the disclosures made herein.

For example, animals in which Cushing's is suspected can be administered a premeasured dose of glucagon. Blood can then be collected at one or more select points in time, e.g., at 15, 30 and 60 minutes after injection in fluoride-containing tubes (to stop glycolysis) and an analysis using reagent strips for testing glucose levels in whole blood can then be performed immediately as a conclusive test. In the alternative, because reagent strips are sometimes not as sensitive as photometric methods for analysis of glucose, samples in which blood glucose levels are not clearly within the normal ranges can then be subjected to a more accurate analytical determination at a later time without fear of compromising the accuracy of the test.

DESCRIPTION OF THE DRAWINGS

For a fuller understanding of this invention, reference is made to the following description of the preferred embodiments of this invention taken in connection with FIG. 1 (which depicts blood glucose concentrations versus time (in minutes) for three groups of dogs: normal dogs, Cushing's cases and Cushing's analogues.

DESCRIPTION OF THE PREFERRED EMBODIMENTS

The following animal subjects, procedures and exemplary tests are presented as illustrations of my method of diagnosing Cushing's; these tests illustrate the concepts of this invention, but should in no way be regarded as limitations upon those concepts.

TESTS

Use of a glucagon tolerance test to diagnose Cushing's syndrome was evaluated in three groups of dogs. The first group of dogs (Group 1) consisted of 11 normal animals, the second group of dogs (Group 2) consisted of 20 Cushing's dogs, diagnosis confirmed either by ACTH stimulation test or low dose dexamethasone suppression test (LDDS), and a third group of dogs (Group 3) consisted of 12 Cushing's analogues, dogs with clinical signs or laboratory data similar to those seen with Cushing's, i.e., polydipsia-polyuria, diabetes mellitus, endocrine hair loss patterns, abnormal biochemistry data (elevation in serum alkaline phosphatase levels). Dogs in all groups received the following workup: ACTH stimulation test, low dose dexamethasone suppression test, complete blood count, serum chemistry profile, urinalysis and glucagon tolerance test. Since either abnormal ACTH response test or low dose dexamethasone suppression tests are considered recognized criteria for the diagnosis of Cushing's in the dog, the glucagon tolerance test was compared against these tests. The results of these tests are depicted in FIG. 1. The mean and standard deviation values at select points in time over the two hour test period were as follows:

| Glucose mg/dl | 0 | 5 | 15 |
|---|---|---|---|
| Group 1 | 116 ± 22.9 | 226 ± 61.3 | 317 ± 58 |
| Group 2 | 109.2 ± 56.2 | 192 ± 73.9 | 233.8 ± 74 |
| Group 3 | 95.6 ± 8.2 | 170.7 ± 29 | 212.2 ± 44.6 |
| Glucose mg/dl | 30 | 60 | 120 |
| Group 1 | 363 ± 78.6 | 317.8 ± 86.3 | 146.4 ± 561 |
| Group 2 | 244 ± 92.7 | 174.3 ± 104.2 | 130.8 ± 80.9 |
| Group 3 | 184 ± 58.6 | 114 ± 28.4 | 94.9 ± 6.3 |

FIG. 1 and the above table indicates that peak measured glucose values of about 295 mg/dl are significant.

That is, twenty of twenty Cushing's dogs had glucoses values greater than 295 mg/dl. Zero of eleven normal dogs had greater than 295 mg/dl and zero of twelve Cushing's analogues were greater than 295 mg/dl. This data indicates that a peak glucose value of 295 following glucagon administration is diagnostic for Cushing's in the dog.

The following results compare the glucagon tolerance test with the ACTH stimulation test and low dose dexamethasone suppression (LDDS) test as diagnostic screens for Cushing's. Twenty of twenty Cushing's dogs showed an abnormal ACTH response or an abnormal LDDS. Thirteen of twenty showed both an abnormal ACTH response and an abnormal LDDS test. Five of twenty of the LDDS tests were nondiagnostic. Two of twenty ACTH response tests were nondiagnostic. However, twenty of twenty of Cushing's dogs had glucose values greater than 295 mg/dl. Consequently these results also indicate that the glucagon tolerance test can identify Cushing's dogs from normal animals in an accurate, technically simple and economic advantageous test.

Glucagon Treatment Reference Curves. Glucagon treatment reference curves for normal dogs were determined using a wide range of pharmacologic doses of glucagon in dogs in various age groups: the doses being 0.14 mg/kg (5 adult dogs) and 0.03 mg/kg (11 adult dogs) and (3 juvenile dogs). A reference curve was established for a horse using a dose of 0.03 mg/4.5 kg or 0.00074 mg/kg. All animals were fasted for 24 hours prior to establishing their respective reference curve and were considered normal by all available clinical and biochemical means. Significant to the normal curve is the peak of blood glucose values at about 15 minutes. Note also that despite the wide range of glucagon used in the reference group, peak levels of glucose following IV injections are similar for both test groups of dogs and are markedly similar for other animals such as the horse and cat.

LABORATORY EXAMINATION

Blood samples were collected with an 18-gauge jugular catheter. All samples were collected between 0830 and 1205 hours. Collection times were standardized such that each sample for a particular dog was collected at the same time. Those samples requiring serum were allowed to stand for 15 minutes and were centrifuged, and the serum was separated. Serum chemical profiles and blood glucose determinations were performed on an automated chemistry analyzer (Rotochem IIa, Travenol Laboratories, Inc., Instrument Division, Savage, Md.) at 1230 hours. Serum cortisol was quantified by validated radioimmunoassay procedure. The CBC were performed with the aid of a Coulter counter.

GLUCOSE TESTS

Serum glucose values (see FIG. 1) during the glucagon tolerance test (0.03 mg/kg, IV) were determined at 0, 5, 15, 30, 60, 90 and 120 minutes after glucagon administration by use of an automated chemistry analyser (Rotochem II, Travenol Laboratories, Inc., Instruments Division, Savage, Md.). Statistical analysis was completed on a data processing computer system (Eclipse M/600, Data General Corp., West Borough, Mass.) using paired t tests.

These glucagon tolerance test results indicate that it is a sensitive indicator of altered carbohydrate metabolism and hepatic glycogen accumulation. Consequently, the test could be useful in detecting hepatic alteration as a result of hyperglucocorticism due to Cushing's syndrome. Seemingly, a complete glucagon tolerance test may not be warranted. A sample for blood glucose determination could be taken before and 30 minutes after glucagon stimulation. Therefore these tests can be used as a sensitive indicator of Cushing's. In general, however, the above data indicates that absolute blood glucose levels of greater than about 295 mg/dl especially in the time period between about 15 and about 60 minutes after glucagon injection, is diagnostic of Cushing's syndrome. The time period at about 30 minutes after injection is the peak region of the blood glucose value. Normal dogs, for example, characteristically do not have blood glucose values of greater than about 262 mg/dl; and these peak at about 15 minutes. Therefore, all things considered, and in the absence of exogenous glucocorticoid administration to the animal, a glucose value above about 295 mg/dl at any sample time can be taken as positive evidence of Cushing's syndrome.

It should also be noted that the concentrations of the glucagon to establish reference curves such as those in FIG. 1, and the glucagon used in the glucagon tolerance test itself may be used in wide ranges of concentrations. In the case of dogs a dose of about 0.03 mg/kg will suffice. Moreover, the times over which such reference curves are established and the dose level at which the animal is challenged can be varied over substantial ranges, if desired. Test periods of less than about 2 hours are preferred, and test periods less than about 1 hour are more preferred. Any number of blood samples may be taken over such test periods. It is also within the scope of the teachings of this invention that a single blood sample be used to establish supraphysiological glucocorticoid levels and hence diagnose Cushing's. The determination of the frequency of such test is well within the ability of those skilled in the art. It should be specifically noted, however, that the taking of a blood sample from dogs after about fifteen minutes and before about 60 minutes from the glucagon administration is a highly preferred embodiment of this invention. Those skilled in the art will also appreciate that this test may be carried out by a variety of glucagon tolerance test equipment and procedures, e.g., digitized equipment having LED readouts, wet-chemistry indicators, etc. However, for field use, a simple glucose indicator tape, preferably one designed to show a positive reading above about a 295 mg/dl blood glucose level, would represent a highly preferred embodiment of the method and the most simple apparatus for carrying out the method of this invention. Perhaps the most convenient apparatus to carry out the method of this invention in the field would be a kit comprised of a premeasured glucagon loaded hypodermic syringe or ampul, a catheter and fluoride containing tubes to inhibit glycolysis for collecting samples of the animal's blood and a glucose indicator tape having a positive indicator at a blood glucose level of about 295 mg/dl. Those skilled in the art will appreciate that the methods of this invention may be carried out with apparatus elements other than those suggested for the above field use kit without departing from the scope and spirit of this invention. That is to say, the applicant's invention is not to be limited by the specific concentrations, test times, glucagon levels, administration or collection equipment specified herein. On the contrary, many changes may be made carrying out the above methods without departing from the spirit and scope of the invention. For example, blood glucose levels may be determined by a variety of instruments other than glucose indicator types such as, for example, photometric devices having LED readouts. Therefore, it is intended that all matter contained in the above description shall be interpreted as illustrative and not in a limiting sense. It is also to be understood that the following claims are intended to cover all of the generic and specific features of the invention herein described, and all statements of the scope of the invention, which, as a matter of language, might be said to fall there between.

Thus having disclosed the invention, what is claimed is:

1. A method for diagnosing Cushing's Syndrome in animals, said method comprising the steps of:
    (a) administering a pharmaceutical dose of glucagon to an animal suspected of having Cushing's Syndrome;
    (b) taking a blood sample from the animal between about 15 and about 60 minutes after administration of the glucagon;
    (c) exposing the blood sample to a test which compares the blood glucose level of the sample to an indicator of blood glucose level which is capable of indicating a blood glucose level greater than about 295 mg/dl; and
    (d) noting a blood glucose level greater than about 295 mg/dl and thereby diagnosing Cushings's Syndrome in the animal.

2. A method for diagnosing Cushing's Syndrome in an animal, said method comprising the steps of:
    (a) establishing a reference curve for blood glucose levels whose values are indicative of the existence of Cushing's Syndrome in the animal;
    (b) administering a pharmacological dose of glucagon to the animal suspected of having Cushing's syndrome;
    (c) taking one or more blood sample(s) from the animal over a time period from about 15 to about 60 minutes;
    (d) determining the blood glucose level of the sample(s);
    (e) comparing the blood glucose level of the sample(s) to the blood glucose level(s) found in the reference curve to determine whether there is a blood glucose level which is indicative of Cushing's Syndrome in said animal.

3. The method of claim 2 wherein the time period used in establishing the reference curve is less than about one hour.

4. The method of claim 2 wherein the blood samples are taken at about 15, 30 and 60 minutes after administering the glucagon.

5. The method of claim 2 wherein the blood sample is taken at about 30 minutes after administering the glucagon.

* * * * *